United States Patent
Roth et al.

(10) Patent No.: US 8,105,410 B2
(45) Date of Patent: *Jan. 31, 2012

(54) WATER DISSIPATION DEVICE WITH CAPILLARY ACTION

(75) Inventors: Gary James Roth, Wake Forest, NC (US); Daniel Patrick Dwyer, Raleigh, NC (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 756 days.

This patent is subject to a terminal disclaimer.

(21) Appl. No.: 12/145,902

(22) Filed: Jun. 25, 2008

(65) Prior Publication Data

US 2009/0020116 A1  Jan. 22, 2009

Related U.S. Application Data

(63) Continuation-in-part of application No. 11/826,597, filed on Jul. 17, 2007.

(51) Int. Cl.
*B01D 46/00* (2006.01)

(52) U.S. Cl. .............. 55/486; 55/498; 55/503; 55/504

(58) Field of Classification Search .............. 96/4, 108, 96/124, 125, 150; 55/309, 312, 314, DIG. 33, 55/DIG. 34; 95/46, 52; 128/205.29, 205.27, 128/203.16, 202.13; 261/104, 107

See application file for complete search history.

(56) References Cited

U.S. PATENT DOCUMENTS

| | | | |
|---|---|---|---|
| 3,747,598 A | 7/1973 | Cowans | |
| 4,172,709 A | 10/1979 | Kippel et al. | |
| 4,200,094 A | 4/1980 | Gedeon et al. | |
| 4,232,667 A | 11/1980 | Chalon et al. | |
| 4,355,636 A * | 10/1982 | Oetjen et al. | 128/204.13 |
| 4,548,626 A | 10/1985 | Ackley et al. | |
| 5,035,236 A | 7/1991 | Kanegaonkar | |
| 5,131,387 A * | 7/1992 | French et al. | 128/205.27 |
| 5,195,527 A | 3/1993 | Hicks | |
| 5,230,727 A | 7/1993 | Pound et al. | |
| 5,460,172 A | 10/1995 | Eckerbom et al. | |
| 5,505,768 A | 4/1996 | Altadonna | |
| 6,415,788 B1 | 7/2002 | Clawson et al. | |
| 6,550,476 B1 | 4/2003 | Ryder | |
| 6,662,802 B2 * | 12/2003 | Smith et al. | 128/203.16 |
| 6,792,946 B1 | 9/2004 | Waldo, Jr. et al. | |

(Continued)

FOREIGN PATENT DOCUMENTS

WO    WO 99/60954 A1    12/1999

(Continued)

*Primary Examiner* — Duane Smith
*Assistant Examiner* — Karla Hawkins
(74) *Attorney, Agent, or Firm* — Baker & Hostetler LLP

(57) ABSTRACT

A water dissipation device for a breathing circuit is provided, including a bucket-shaped hollow composite structure having walls made of a first inner layer made of water vapor wicking material, and a second outer layer of a water vapor breathable medium surrounding the first inner layer. The device defines a flow space surrounded by the composite structure to provide a superior way of removal of moisture or water vapor from a breathing circuit, due to the greater surface area of flow spaces bounded by a water vapor breathable medium and the use of a water vapor wicking material and relatively long dwell times and flow paths through the device. The result is that when the device is connected to a breathing circuit, rainout or condensation in the breathing tube and collection of water within the breathing circuit is significantly reduced.

15 Claims, 15 Drawing Sheets

U.S. PATENT DOCUMENTS

| | | |
|---|---|---|
| 6,976,488 B2 | 12/2005 | Halperin |
| 7,140,366 B2 | 11/2006 | Smith et al. |
| 2001/0054422 A1 | 12/2001 | Smith et al. |
| 2002/0002976 A1 | 1/2002 | Smith et al. |
| 2004/0123974 A1 | 7/2004 | Marler et al. |
| 2005/0121074 A1 * | 6/2005 | Pittaway et al. ............... 137/171 |

FOREIGN PATENT DOCUMENTS

| | | |
|---|---|---|
| WO | WO 2005/047797 A2 | 5/2005 |

* cited by examiner

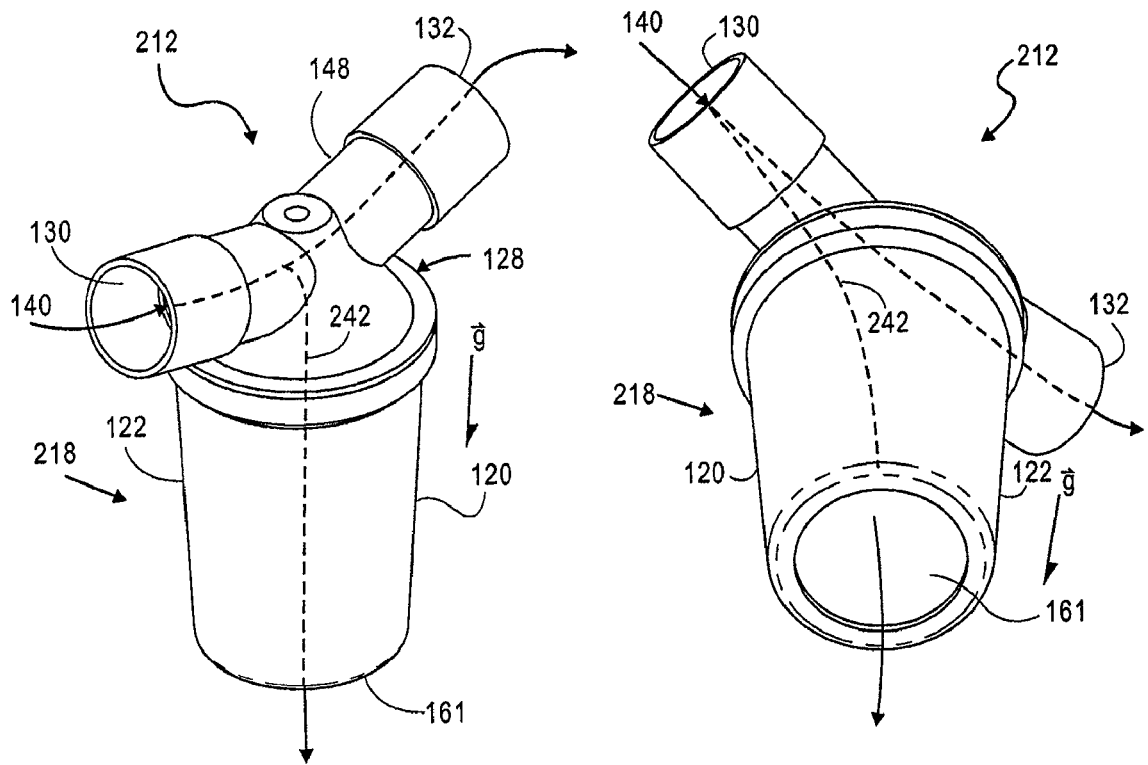
FIG. 9
FIG. 10
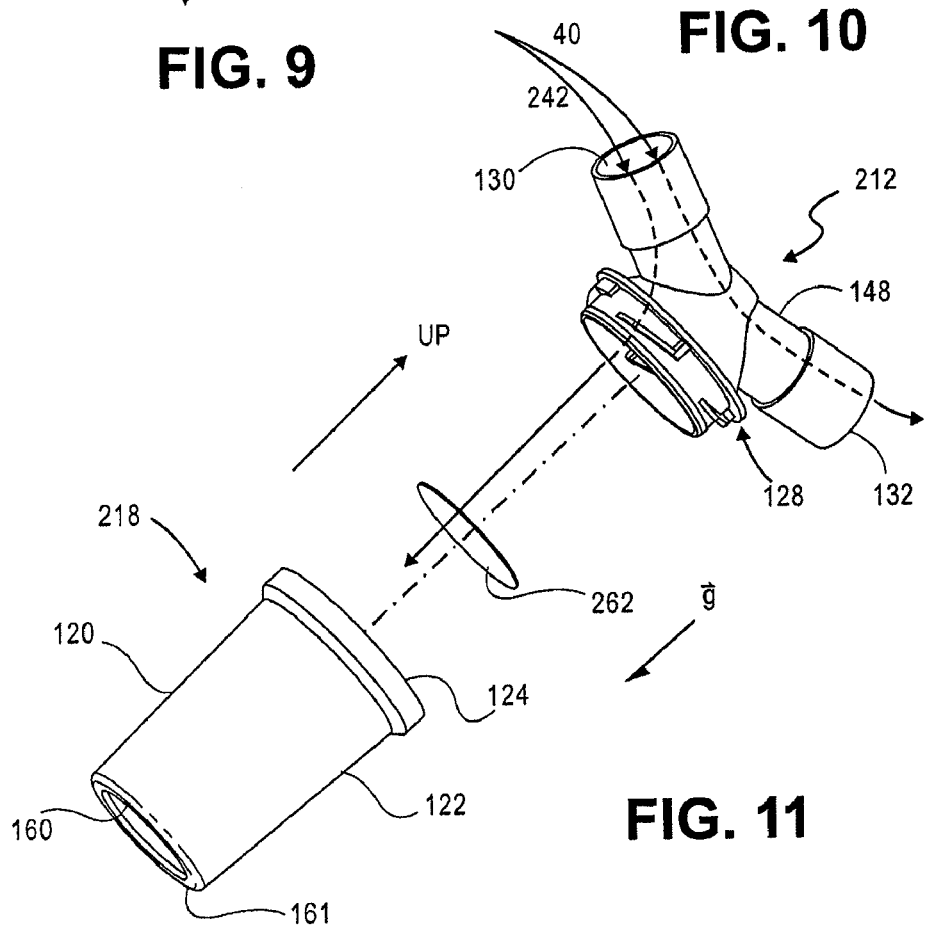
FIG. 11

WATER DISSIPATION DEVICE WITH CAPILLARY ACTION

CROSS-REFERENCE TO RELATED APPLICATIONS

The present application claims priority to and is a continuation-in-part of U.S. application Ser. No. 11/826,597, filed Jul. 17, 2007, now pending, the entire contents of which are incorporated herein by reference.

FIELD OF THE INVENTION

The present invention relates generally to a medical device. More particularly, the present invention is related to a water dissipation device for placement in a breathing circuit.

BACKGROUND

A breathing circuit delivers medical gas to a patient under pressure in a prescribed volume and breathing rate. The medical gas is often humidified by a humidifier located at or near the ventilator or respirator. The optimum respiratory circuit delivers 100% RH medical gases @ 35 to 39 degrees C. to the patient while reducing the amount of humidity and subsequent condensate delivered back to the ventilator through the expiratory limb. Therefore, the humidified gas has to travel through all or most of the tubing and has time to cool. Cooling of the gas leads to rainout or condensation in the breathing tube and collection of water within the breathing circuit.

Several solutions to the problem of rainout have been developed. One such solution is a heating wire provided along the length of the tube. The wire may be provided within the interior of the tubing or alternatively may be embedded along the interior of the tubing. The wire heats the humidified gas traveling through the tubing to prevent the gas from cooling, thus preventing the problem of water condensing out of the gas traveling through the breathing circuit. However, the manufacture of such heated wire respiratory circuits can be time consuming and costly.

Another such solution, which eliminates the heated wire, is to provide a water collection device somewhere within the breathing circuit. A water collection apparatus is typically placed in the expiratory limb of the respiratory circuit in front of the ventilator or respirator to collect and manually remove excessive condensation prior to the gases entering the ventilator or respirator. It is known that excessive condensate entering a ventilator or respirator from the expiratory limb of a respiratory circuit can harm the device.

Most frequently, the water collection device is designed to trap the condensed water vapor in a removable container. When the container is removed, a valve can be actuated to create a gas tight seal for the breathing circuit. However, this type of water collection device has to be monitored and manually emptied, causing risk of patient or caregiver infection.

Accordingly, it is desirable to provide an improved apparatus for removing or decreasing water vapor or condensate in a breathing circuit. It is further desirable that the improved apparatus for removing water vapor or condensate from the breathing tube reduce or eliminate the need to heat the exhalation limb of the breathing tube and the need to use currently known water collection or other dissipation devices.

SUMMARY

The foregoing needs are met, to a great extent, by the present invention, wherein an apparatus is provided that in different embodiments provides an improved water dissipation device for placement in a breathing circuit where said water dissipation device will eliminate the need to use a secondary water collection device or manually remove the water condensate and will instead allow for removal of water vapor from the circuit through osmosis. The device includes in one embodiment a hollow composite structure having walls made of different layers including a water vapor wicking material and water vapor breathable medium, which structure at least partially bounds an inner flow space defined by the device providing an extended area and dwell time for moisture in humidified gases to travel through the composite structure and thereby be removed from the flow in a breathing circuit to which the device is coupled.

In one embodiment of the present invention, a water dissipation device for a breathing circuit is provided, including an entry port and an exit port for coupling the device to the breathing circuit. The entry port receives fluid flow from the breathing circuit. The device further defines an inner flow space fluidly coupled to the entry port and exit port. A cover structure partially bounds the inner flow space and includes an inner layer partially bounding the inner flow space. The inner layer is made of water vapor wicking material. An outer layer is over the inner layer. The outer layer is made of a water vapor breathable medium.

In another embodiment of the present invention, a water dissipation device for a breathing circuit is provided, including a cover partially enclosing a flow space and having at least two layers. The cover includes a first inner layer made of water vapor wicking material, and a second outer layer surrounding the first inner layer, the second outer layer made of a water vapor breathable medium. An entry port fluidly couples the flow space to the breathing circuit. The flow space is at least partially bounded by the first inner layer. The entry port, flow space and cover provide a flow path for water vapor out of the breathing circuit.

In yet another aspect of the present invention, a water dissipation device for a breathing circuit is provided, including a bucket-shaped hollow composite cover structure defining a top opening and closed bottom and having walls made of a first inner layer made of water vapor wicking material, and a second outer layer surrounding the first inner layer, the second outer layer made of a water vapor breathable medium. An upper lid covers said top opening and has an entry port for receiving flow from a breathing circuit. An inner frame structure is disposed inside a volume enclosed by the cover structure between the upper lid and closed bottom of the cover structure. The cover structure encloses a flow space for receiving flow from the entry port. The flow space is bounded by the upper lid, the first inner layer and the inner frame. The flow space is in fluid communication with the entry port and provides a flow path for water vapor from said entry port through said cover structure to exit the device.

There has thus been outlined, rather broadly, certain embodiments of the invention in order that the detailed description thereof herein may be better understood, and in order that the present contribution to the art may be better appreciated. There are additional embodiments of the invention that will be described below and which form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 9 is a three-quarter view illustrating another embodiment of the present invention;

FIG. 10 is a bottom view of the embodiment illustrated in FIG. 9;

FIG. 11 is an exploded view of the embodiment illustrated in FIGS. 9 and 10;

DETAILED DESCRIPTION

Figure 1:
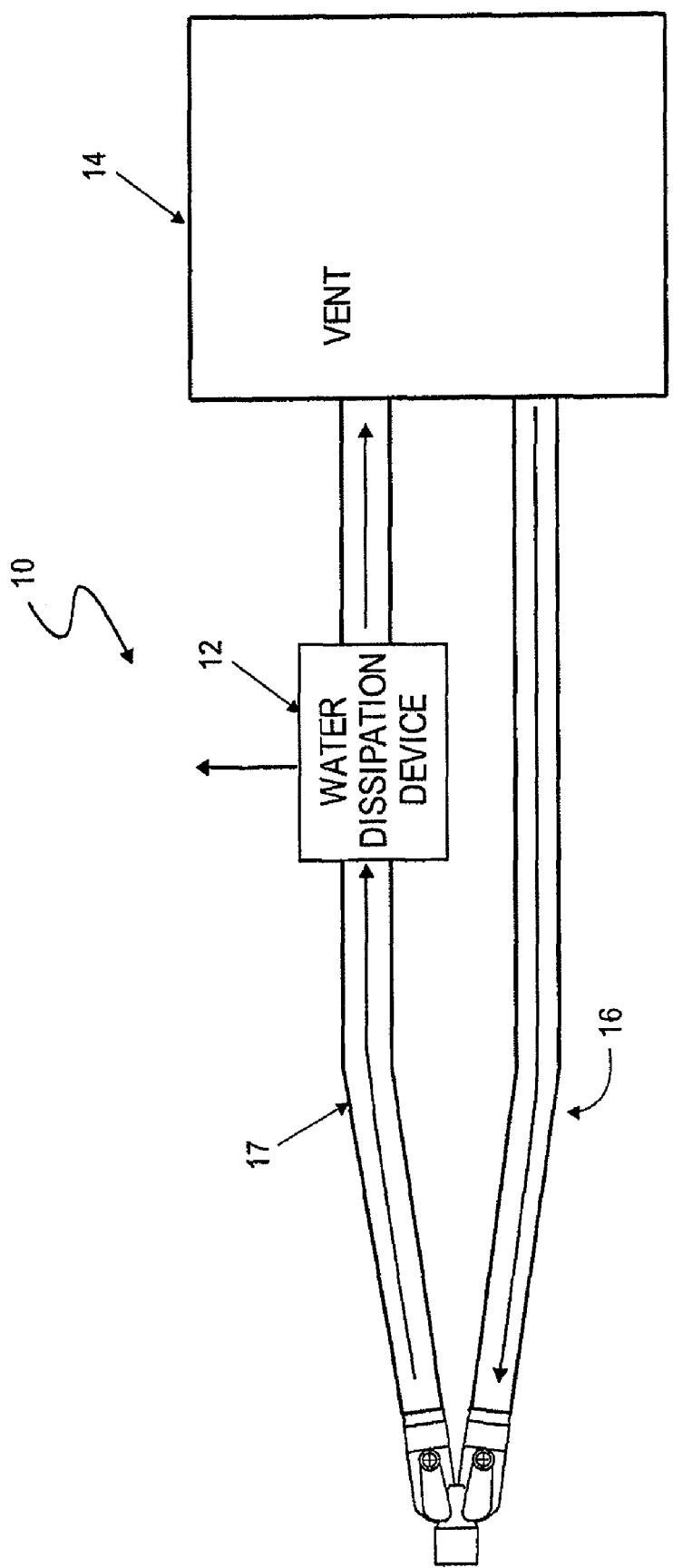
FIG. 1 is a schematic view illustrating a breathing circuit.

The invention will now be described with reference to the drawing figures, in which like parts are referred to with like reference numerals throughout. An embodiment in accordance with the present invention provides a water dissipation device to remove water vapor or condensate from a humidified medical gas traveling through a breathing circuit between a ventilator and a patient or the patient and the ventilator. The present invention includes a water dissipation device having a housing defining entry and exit ports for coupling to the breathing circuit and a breathable medium permeable to water vapor and impermeable to liquid water, viruses and bacteria enclosed within said housing.

FIG. 1 is a schematic view illustrating a breathing circuit 10 including a water dissipation device 12. The water dissipation device 12 is placed in the breathing circuit 10 between a ventilator 14 and a breathing tube 17 from a patient. The breathing circuit 10 is completed by a second breathing tube 16 extending between the patient and the ventilator. The breathing circuit 10 is a closed system wherein liquid water and/or gases are not able to enter or leave the breathing circuit, except for the release of water vapor. Therefore, the breathing circuit 10 is a closed system except with regard to the passage of water vapor.

Figure 2:
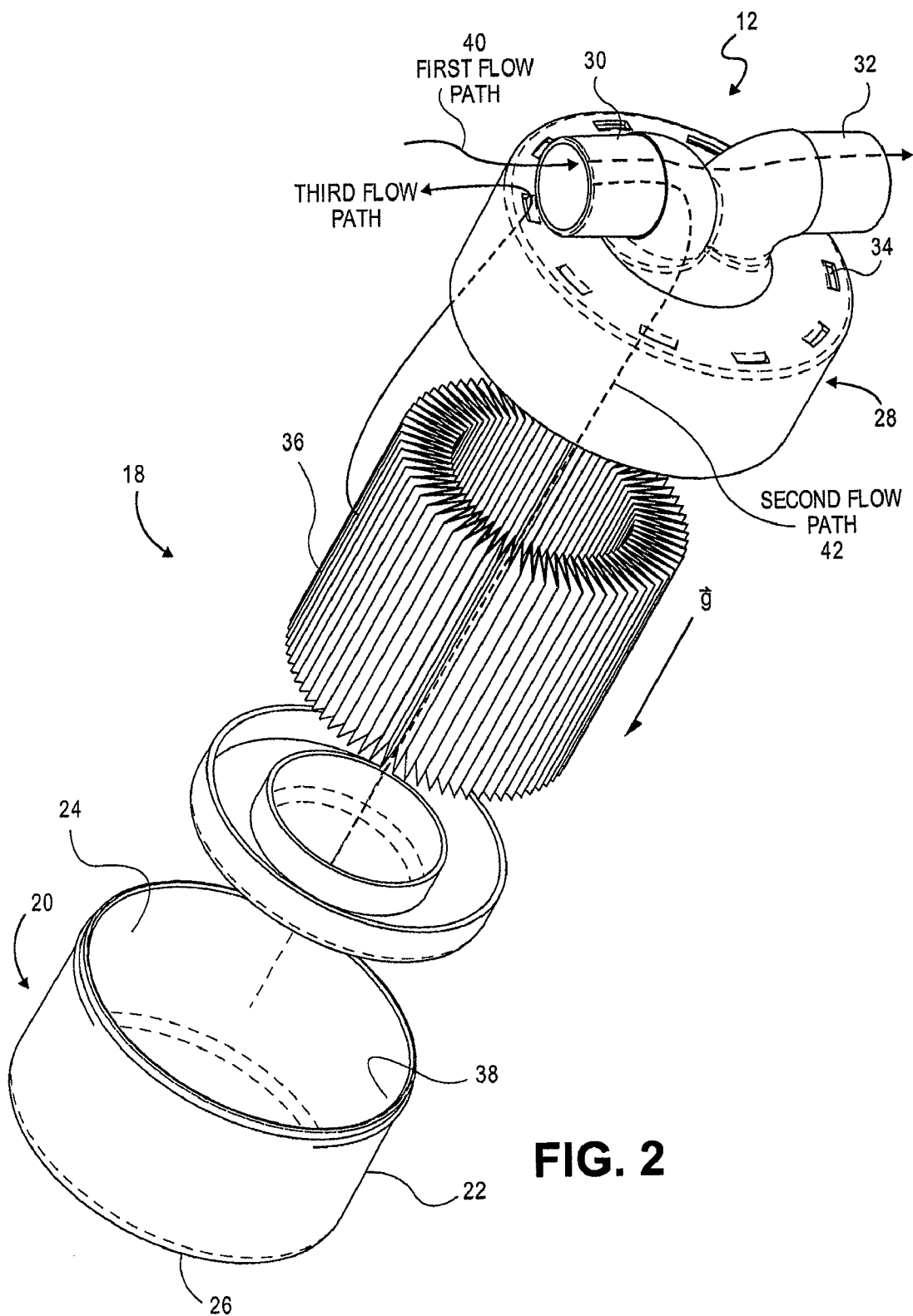
FIG. 2 is an exploded view illustrating a water dissipation device according to an embodiment of the invention.

An embodiment of the present invention is illustrated in FIG. 2. FIG. 2 is an exploded view illustrating the water dissipation device 12 according to a preferred embodiment of the invention. The water dissipation device 12 includes a housing 18 having a cylindrical bottom container 20. The cylindrical bottom container 20 has a side wall 22 that defines a top opening 24 and a bottom surface 26. Also included in the housing 18 is a lid 28 mounted over the top opening 24. The housing 18 defines an entry port 30 and an exit port 32, and more specifically the lid 28 defines the entry port 30 and the exit port 32. The entry port 30 and the exit port 32 allow the water dissipation device 12 to be connected to a breathing circuit, such that the entry port 30 is connected to an expiratory limb of a breathing tube from the patient and the exit port 32 is connected to the rest of the same breathing tube directed toward a ventilator. As shown in FIG. 2, water vapor vents 34 are defined by the housing 18, and more specifically are defined along a periphery of the lid 28. A plurality of the water vapor vents 34 are disposed around an outer edge of a top surface of the lid 28. The lid 28 can also be manufactured from a thermally conductive material to facilitate the cooling of the respiratory gases and increase water condensation, An annular or tubular breathable medium 36 is enclosed in the housing 18. The tubular breathable medium 36 may be pleated to increase the surface area of the breathable medium within the housing 18. The breathable medium 36 may also line at least a portion of an inside surface 38 of the side wall 22. As used herein, a "breathable medium" is formed of a material that is permeable to water vapor and impermeable to liquid water and gases other than water vapor. The breathable medium 36 allows water vapor to exit the water dissipation device while eliminating the need to open the water dissipation device to empty a reservoir of water and, therefore, allows the system to remain closed.

Figure 3:
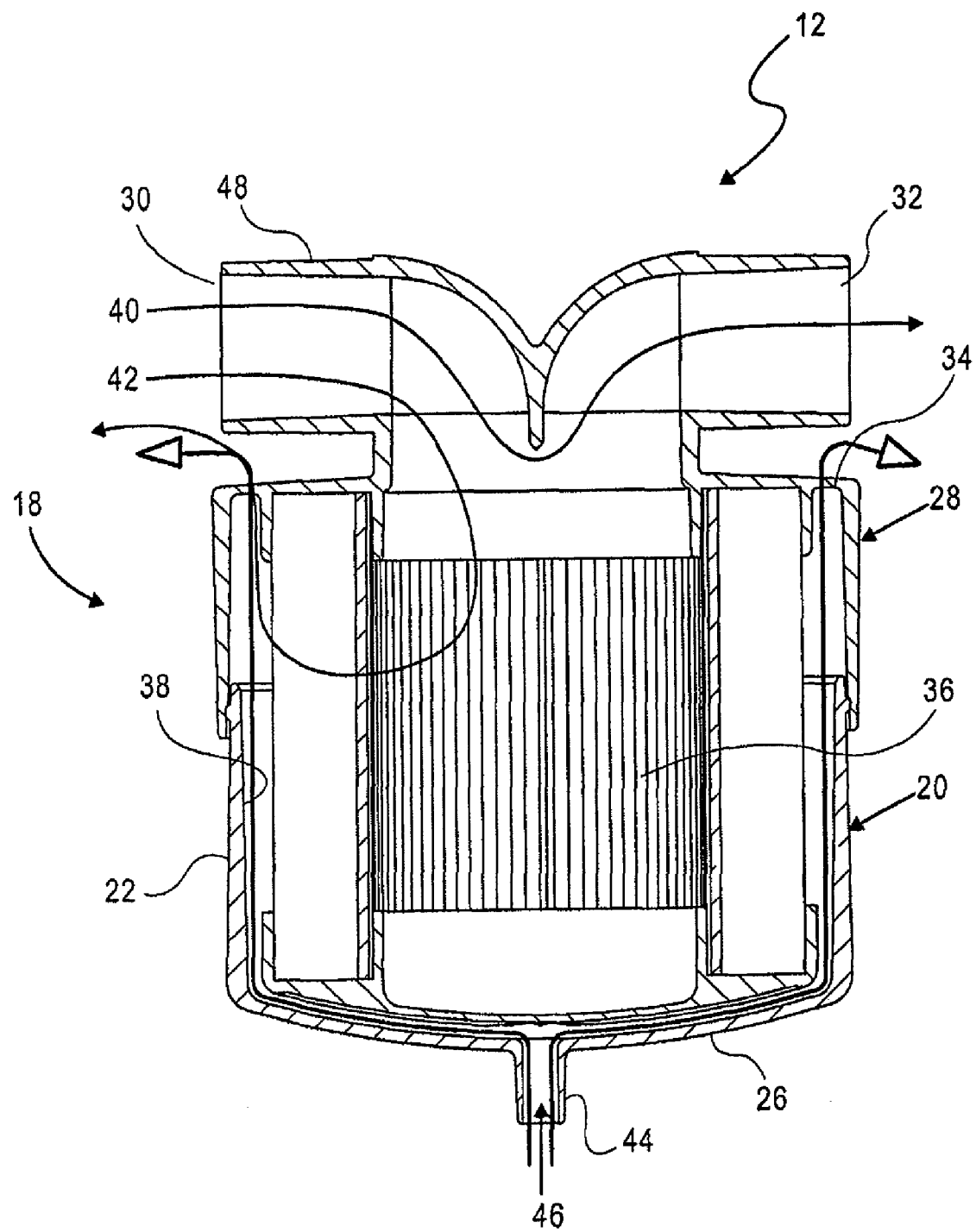
FIG. 3 is a cross sectional view illustrating the embodiment of the water dissipation device illustrated in FIG. 2.

FIG. 3 is a cross sectional view that further illustrates the embodiment of the water dissipation device illustrated in FIG. 2. The housing 18 defines a first flow path 40 of humidified gas between the entry port 30 and the exit port 32. In the first flow path 40, the humidified gas travels into the water dissipation device 12 via the entry port 30, through the housing 18 and exits the water dissipation device 12 via the exit port 32. The first flow path 40 therefore generally corresponds to the main flow path through the water dissipation device along the breathing circuit.

The housing also defines a second flow path 42 for water vapor that extends from the entry port 30 through the tubular breathable medium 36 to at least one opening defined by the housing, other than the exit port 32. In the embodiment shown in FIGS. 2 and 3, this at least one opening includes the water vapor vents 34 defined by the lid of the housing 18. As shown in FIGS. 2 and 3, in the second flow path 42, water vapor in the humidified gas may permeate through breathable medium 36 and exit through the water vapor vents 34. However, liquid water and other gases cannot permeate the breathable medium 36 and exit through the water vapor vents 34.

Additionally, the bottom surface 26 of the outer housing 18 defines an orifice 44 to connect the water dissipation device 12 to an input air source. The housing 18, therefore, defines a third flow path 46 from the orifice 44 through the water dissipation device 12 and out through the water vapor vents 34. The third flow path 46 provides a route for air introduced by the auxiliary compressed dry air input source to blow condensation off of the breathable medium to reduce liquid water collecting in the water dissipation device, and increase the efficiency of the breathable permeable medium. As can be seen in FIG. 2, the annular or tubular breathable medium 36 defines a central channel 37 within which the second flow path 42 may follow.

Figure 4:
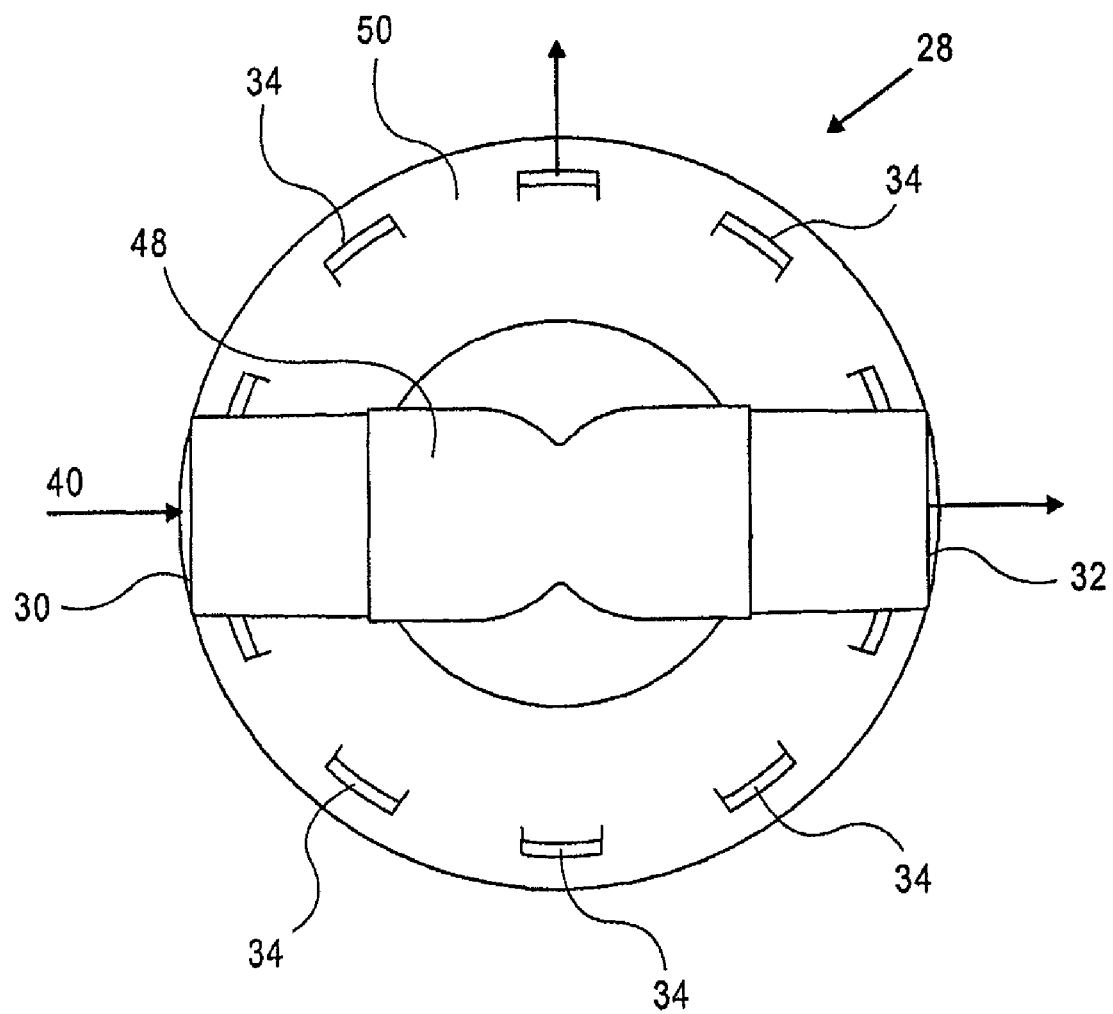
FIG. 4 is a top view of the embodiment of the water dissipation device illustrated in FIGS. 2 and 3.

FIG. 4 is a top view of the lid 28 of the embodiment of the water dissipation device illustrated in FIGS. 2 and 3. FIG. 4 illustrates the entry port 30 and exit port 32 and the water vapor vents 34 in more detail. The entry port 30 and the exit port 32 are disposed on a top surface of the lid 28 and the lid 28 defines a tubular connector portion 48 that couples the water dissipation device 12 to a breathing tube 16. In this embodiment multiple water vapor vents 34 are disposed around the outer edge of the lid 28. However, it is important to note that the number and placement of the water vapor vents 34 are not limited by this embodiment and there may be any number of water vapor vents 34 disposed in any position on the lid 28 or on the remainder of the housing 18.

Figure 5:
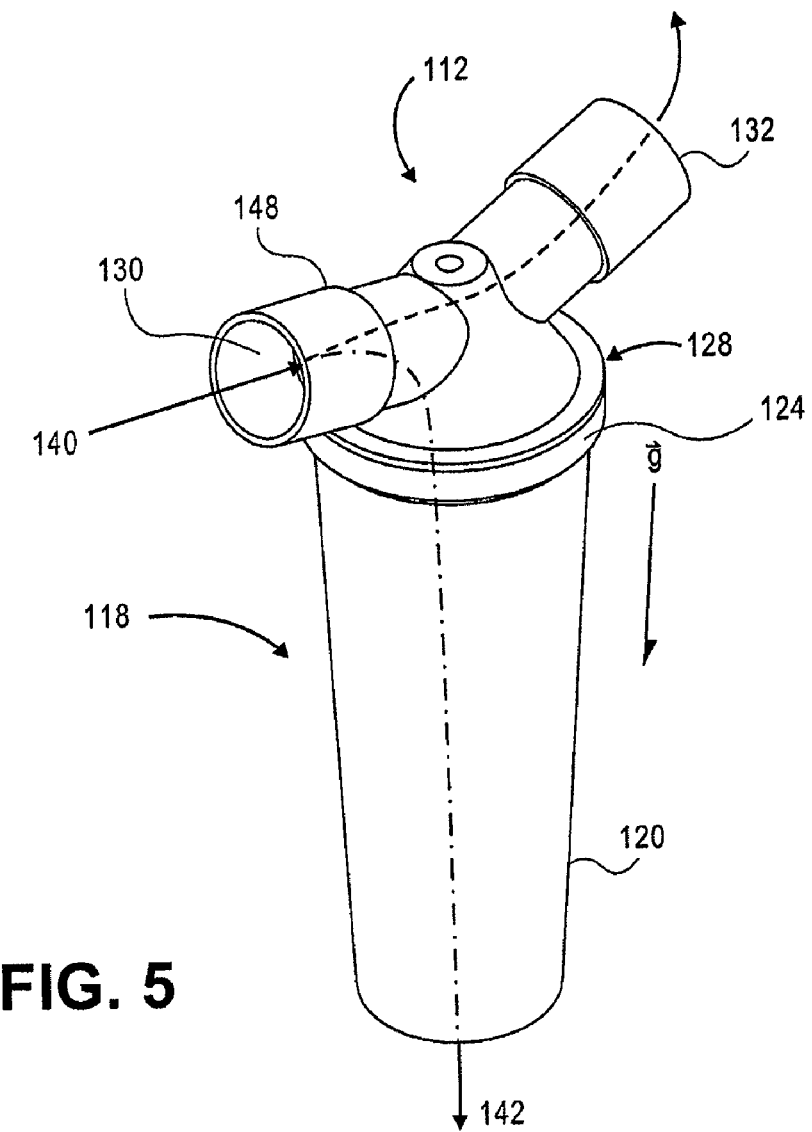
FIG. 5 is a three-quarter view illustrating the water dissipation device according to another embodiment of the present invention.

Another embodiment of the present invention is illustrated in FIG. 5. FIG. 5 is a three-quarter view illustrating a water dissipation device 112 according to another embodiment of the present invention. In this embodiment, the housing 118 includes a cylindrical bottom container 120 that has side wall 122 defining a top opening 124. The housing also includes a lid 128 that is mounted on the top opening 124. Additionally, the housing 118 defines an entry port 130 and an exit port 132.

Figure 6:
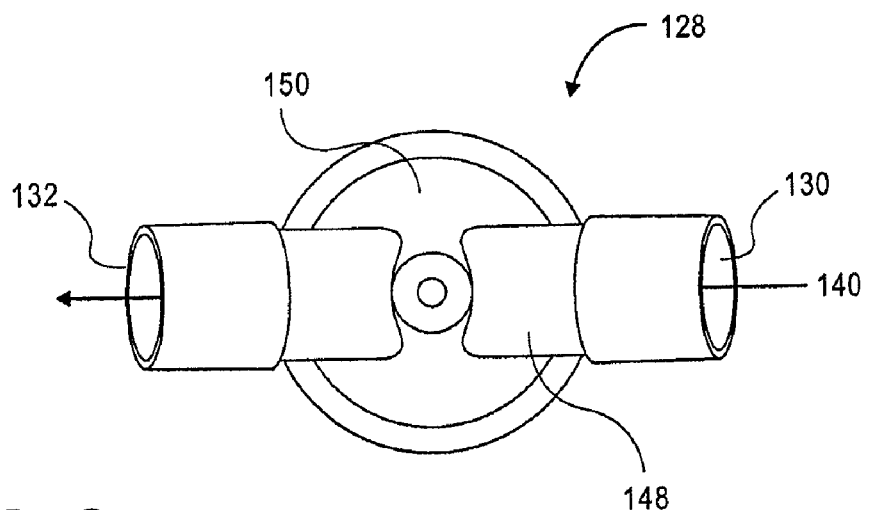
FIG. 6 is a top view of the embodiment illustrated in FIG. 5.

FIG. 6 is a top view of the embodiment illustrated in FIG. 5. FIG. 6 illustrates in more detail the lid 128 and the entry port 130 and the exit port 132. Preferably, the lid 128 is the portion of the housing that defines the entry port 30 and the exit port 132. The entry port 130 and the exit port 132 are disposed on the top surface 150 of the lid 128 and include a tubular connector portion 148 that couples the water dissipation device 112 to a breathing tube.

Figure 7:
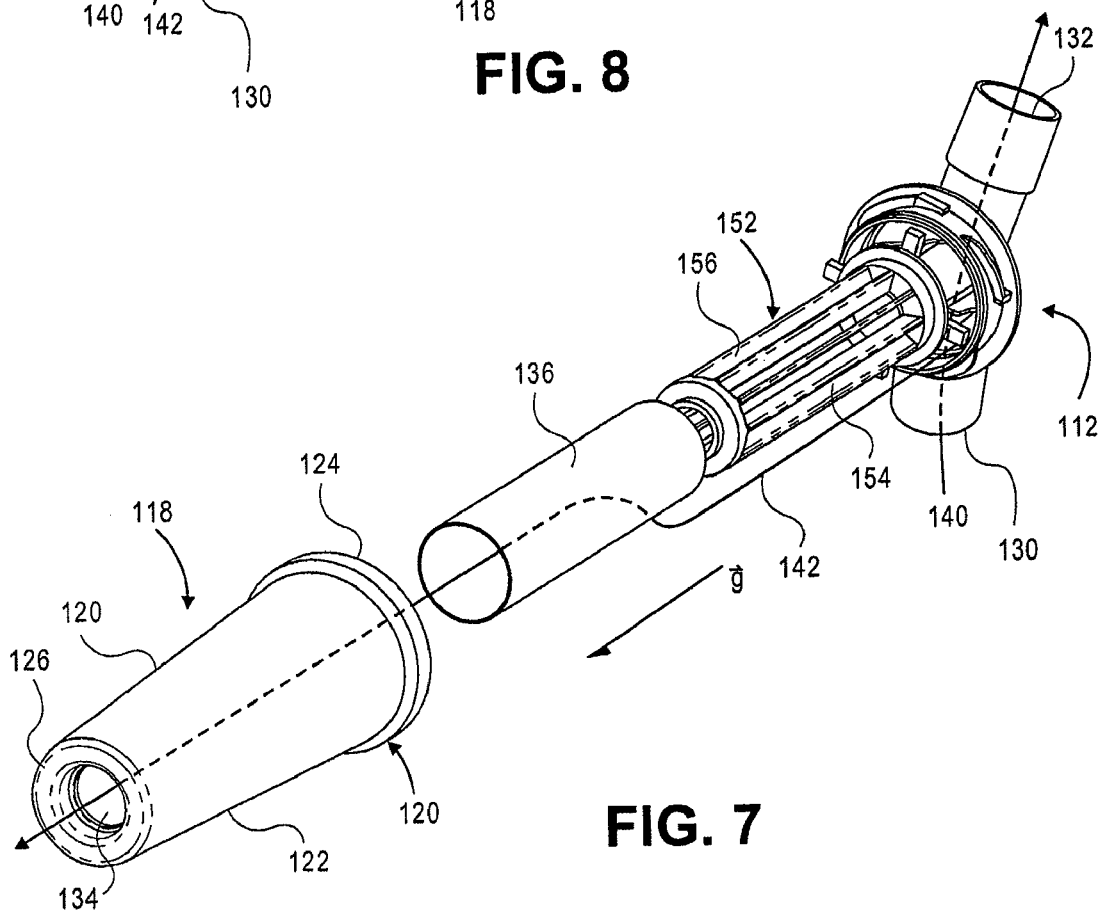
FIG. 7 is an exploded view of the embodiment illustrated in FIGS. 5 and 6.

FIG. 7 is an exploded view of the embodiment illustrated in FIGS. 5 and 6. FIG. 7 illustrates in more detail the structure of the housing 118 and the tubular breathable medium 136. Threads on the lid 128 as well as corresponding threads on the cylindrical bottom container 120 couple the lid 128 to the cylindrical bottom container 120, such that there is an air tight seal between them.

Additionally, the lid 128 has a tubular cage 152 that extends into the cylindrical bottom container 20 of the housing 18. The tubular cage 152 has fins 154 that extend along the span of the housing 118. The fins 154 are separated by longitudinal openings or spaces that define water vapor vents 156 between the fins 154. An annular or tubular breathable medium 136 is also disposed within the cylindrical bottom container 120, and it is positioned between the tubular cage 152 and the sidewalls 122 of the cylindrical bottom container 120 of the outer housing 118.

Figure 8:
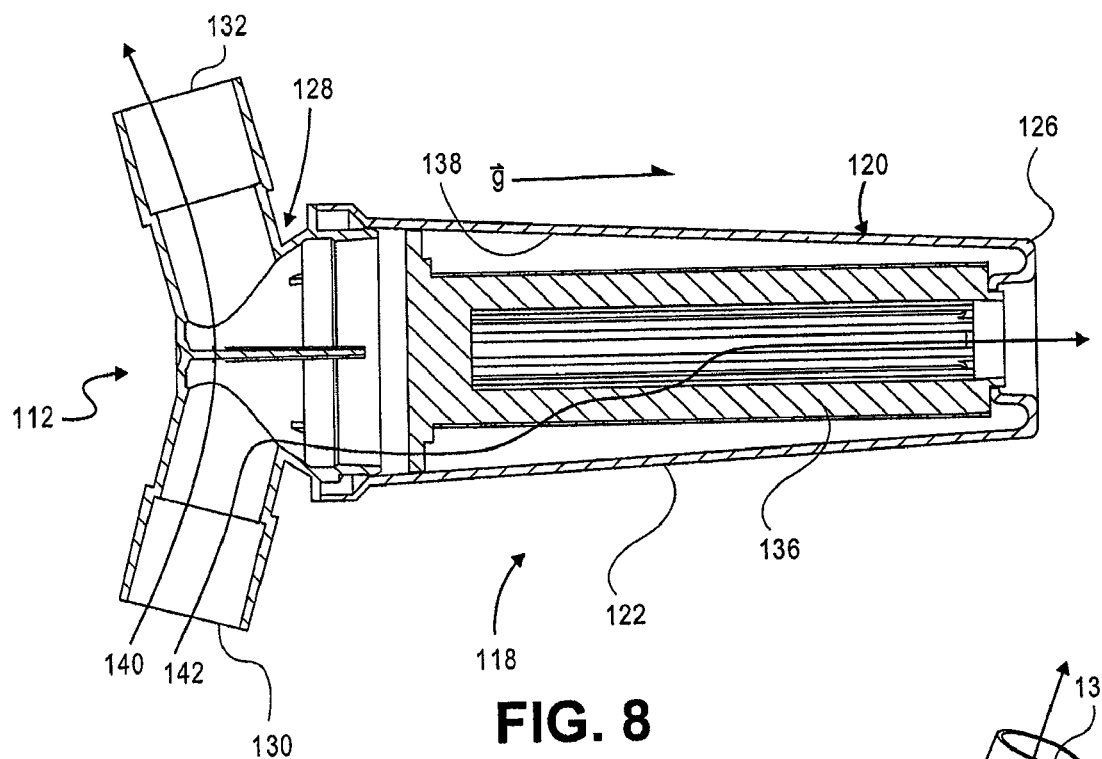
FIG. 8 is a cross sectional view of the embodiment illustrated in FIGS. 5-7.

FIG. 8 is a cross sectional view of the embodiment illustrated in FIGS. 5 through 7. FIG. 8 illustrates the housing 118 and the breathable medium 136 in a fully assembled condition. The lid 128 and the cylindrical bottom container 120 couple together to form an air tight seal. With reference to the gravity vector g shown in FIGS. 7 and 8 for the preferred orientation of the device 112 when inserted into a breathing circuit, the tubular cage 152 extends from a bottom surface of the lid 128 to the bottom surface 126 of the cylindrical bottom container 120. The tubular breathable medium 136 is disposed around and supported by the tubular cage 152.

A first flow path 140 is defined by the housing 118 and extends through the water dissipation device 112 directly from the entry port 130 and through to the exit port 132 as shown in FIGS. 7 and 8. The humidified gas generally flowing through the breathing circuit to which the device of the present invention is attached can therefore travel through the water dissipation device 112 via the first flow path 140. A second flow path 142 is also defined by the housing 118 and extends from the entry port 130 through the tubular breathable medium 136 and out of the water dissipation device 112 via the water vapor vents 156 defined by the fins 154 of the tubular cage 152. Water vapor in the humidified gas may permeate the breathable medium 136 to exit through the water vapor vents 156, but liquid water, bacteria, viruses and other gases cannot permeate the breathable medium 136. It will be noted in FIGS. 7-8 that the second flow path provides for water vapor permeation from the outer surface to the inner surface of the tubular breathable medium 136. Breathable medium 136 defines a central channel 137 through which the final portion of the second flow patent 142 flows.

FIGS. 9, 10 and 11 illustrate another embodiment of the water dissipation device of the present invention. In this embodiment, the housing 218 defines the entry port 130 and exit port 132 for coupling a water dissipation device 212 to a breathing circuit. Preferably, in this embodiment, the housing 218 has a cylindrical bottom container 120 having a side wall 122 that defines a top opening 124. The lid 128 is mounted on the top opening 124 and preferably defines the entry port 130 and the exit port 132. The housing 218 also defines an opening 160 in a bottom surface 161 of the housing 218. A flat disk breathable medium 262 is disposed in said housing 218 and covers the opening 160 in the bottom surface of the housing 218.

A first flow path 140 between the entry port 130 and the exit port 132 is defined by the housing 218. The housing 218 also defines a second flow path 242 from the entry port 130 through the housing 218 and out through the opening 160 and flat disk breathable medium 262 on the bottom surface 161 of the cylindrical bottom container 120. Only water vapor passes through the flat disk breathable medium 262 because it is permeable to water vapor but impermeable to liquid water, bacteria, viruses and other gases.

Figure 12:
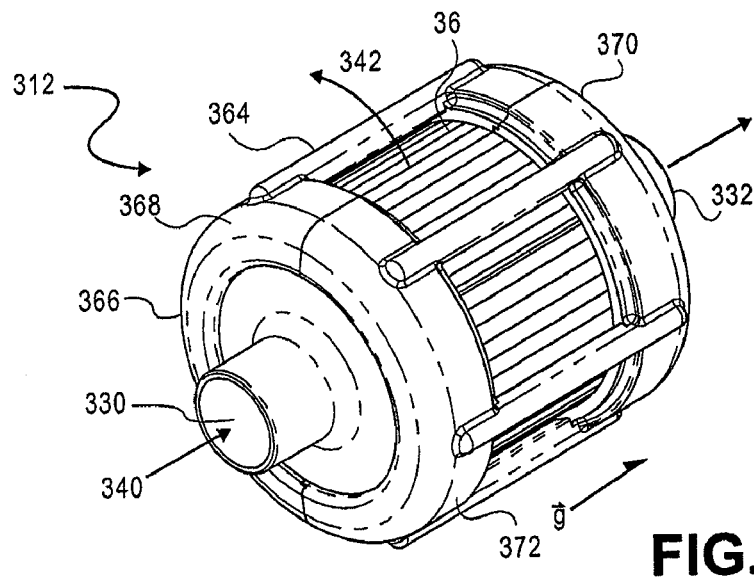
FIG. 12 is a side view illustrating another embodiment of the present invention.
Figure 13:
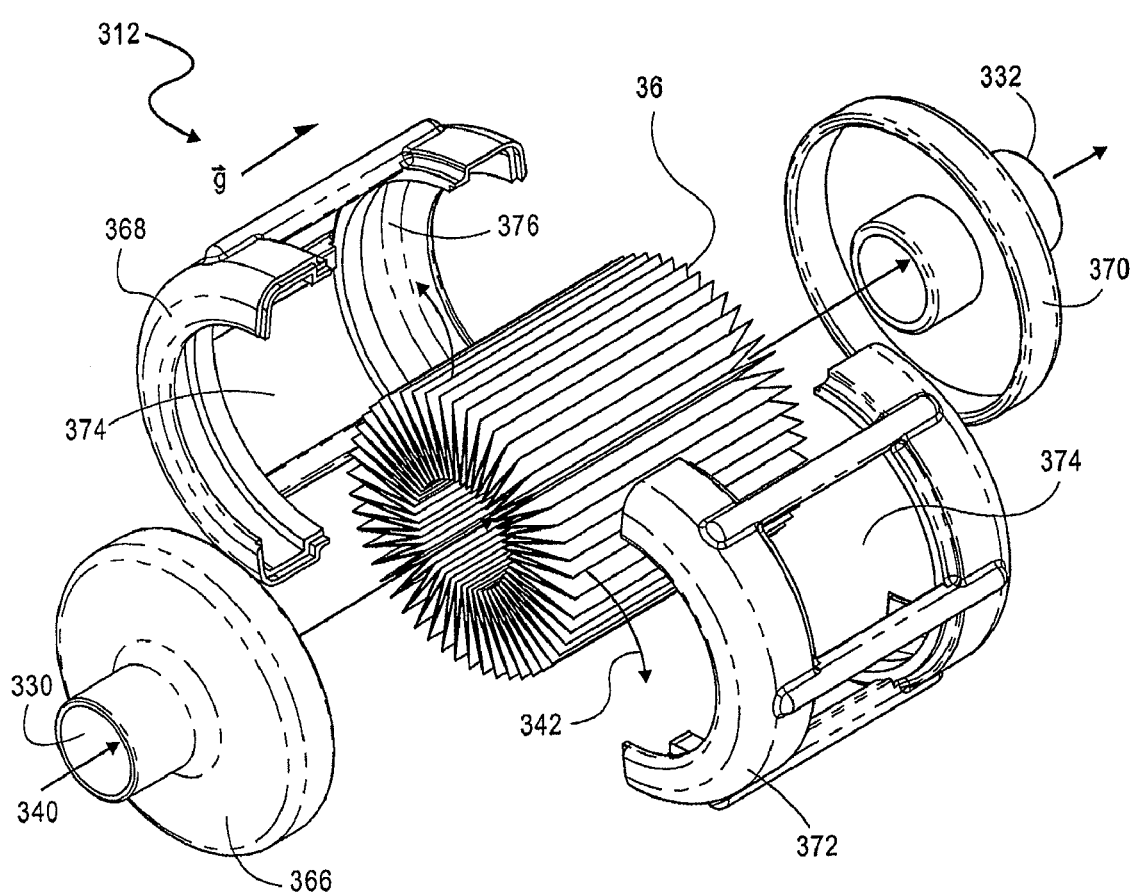
FIG. 13 is an exploded view of the embodiment illustrated in FIG. 12.

FIG. 12 illustrates a side view of another embodiment of the water dissipation device of the present invention. FIG. 13 illustrates an exploded view of the embodiment illustrated in FIG. 12. In this embodiment, a water dissipation device 312 has a cylindrical caged body 364 that encloses an annular or tubular breathable medium 336. The cylindrical caged body 364 is formed of two halves 368 and 372, which can be separable. The water dissipation device 312 has a first end cap 366 defining the entry port 330. A second end portion 370 defines the exit port 332. The circular end caps 366 and 370 are held in place inside complementary grooves on the inside of portions of the caged body halves 368 and 372. A plurality of windows 374 are defined by the cylindrical caged body 364 to allow for egress of water vapor from the water dissipation device 312.

The cylindrical caged body 364 encloses a tubular breathable medium 336 which lines at least a portion of an inside surface 376 of the cylindrical caged body 364. Preferably, the tubular breathable medium 336 is pleated and permeable to water vapor but impermeable to liquid water, bacteria, viruses and other gases. However, the breathable medium 36 should not be limited by this description and may take various forms or positions within the cylindrical caged body 364.

The cylindrical caged body 364 defines a first flow path 340 between the entry port 330 and the exit port 332. Additionally, the cylindrical caged body 364 defines a second flow path 342 from the entry port 330, through the breathable medium 336 and out of the water dissipation device 312 via the windows 374 in the cylindrical caged body 364. Only water vapor passes through the tubular breathable medium 36 in the second flow path 342.

Figure 14:
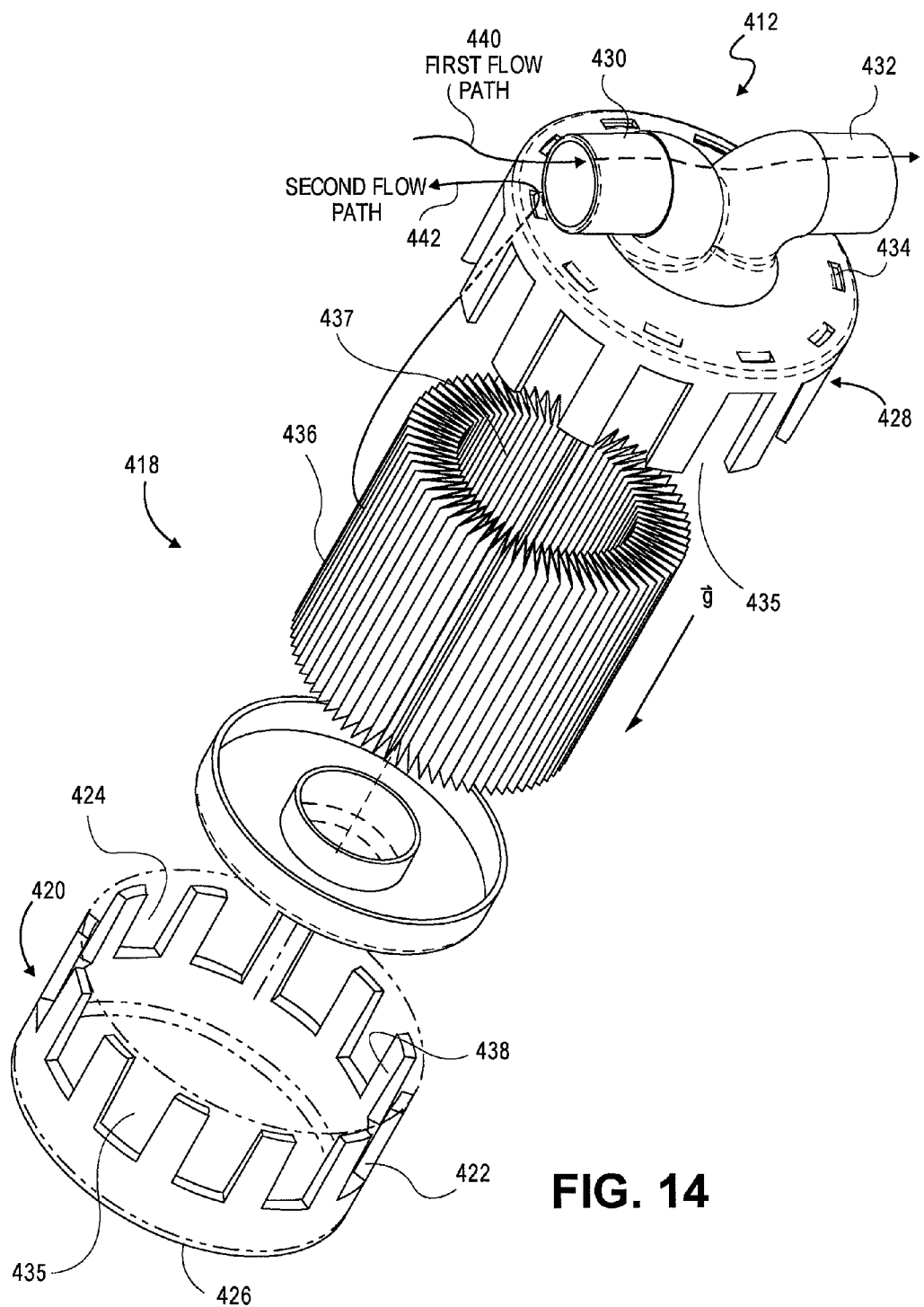
FIG. 14 is an exploded view illustrating another embodiment of the present invention.

An embodiment of the present invention is illustrated in FIG. 14. FIG. 14 is an exploded view illustrating the water dissipation device 412 according to a preferred embodiment of the invention. The water dissipation device 412 includes a housing 418 having a caged cylindrical bottom container 420. The caged cylindrical bottom container 420 has a side wall 422 that defines a top opening 424 and a bottom surface 426. Also included in the housing 418 is a lid 428 mounted over the top opening 424. The housing 418 defines an entry port 430 and an exit port 432, and more specifically the lid 428 defines the entry port 430 and the exit port 432. The entry port 430 and the exit port 432 allow the water dissipation device 412 to be connected to a breathing circuit, such that the entry port 430 is connected to an expiratory limb of a breathing tube from the patient and the exit port 432 is connected to another tube directed toward a ventilator. As shown in FIG. 14, water vapor vents 434 are defined by the housing 418, and more specifically are defined along a periphery of the lid 428. The cylindrical bottom container 420 and the lid 428 also define windows 435 which allow for egress of water vapor from the water dissipation device 412. The lid 428 can also be manufactured from a thermally conductive material to facilitate the cooling of the respiratory gases and increase water condensation.

A tubular breathable medium 436 is enclosed in the caged housing 418. The tubular breathable medium 436 may be pleated to increase the surface area of the breathable medium within the housing 418 and may also be perforated. The breathable medium 436 may also line at least a portion of an inside surface 438 of the side wall 422. The breathable medium 436 is formed of a material that is permeable to water vapor and impermeable to liquid water and other gases. The breathable medium 436 allows water vapor to exit the water dissipation device while eliminating the need to open the water dissipation device to empty a reservoir of water and, therefore, allows the system to remain closed.

Figure 15:
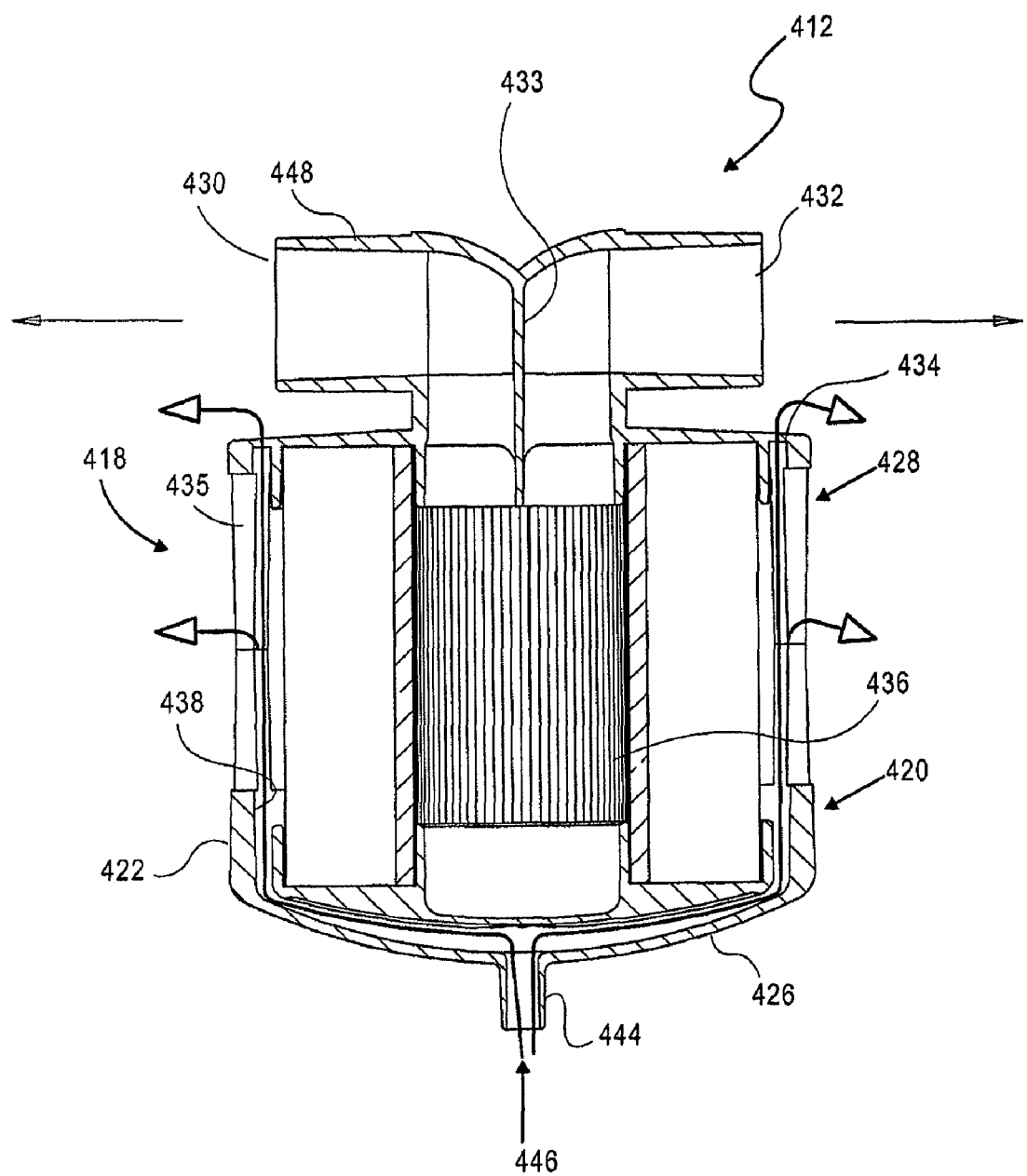
FIG. 15 is a cross-sectional view of the embodiment illustrated in FIG. 14.

FIG. 15 is a cross sectional view that further illustrates the embodiment of the water dissipation device illustrated in FIG. 14. The caged housing 418 defines a first flow path 440 of humidified gas between the entry port 430 and the exit port 432. In the first flow path 440, the humidified gas travels into the water dissipation device 412 via the entry port 430, through the housing 418 and exits the water dissipation device 412 via the exit port 432. The first flow path 440 therefore generally corresponds to the main flow path through the water dissipation device along the breathing circuit, except that in this embodiment, a partition or baffle element 433 extends in the housing 418 perpendicular to the axis through the entry and exit ports 430 and 432, which causes to further define the first flow path 440 to extend farther into the housing 418 and nearer to the channel 437 formed inside the annular breathable medium 436.

The housing also defines a second vapor path 442 that extends from the entry port 430 through the tubular breathable medium 436, and then out to either the water vapor vents 434 defined by the housing 418, or out of the housing 418 through the windows 435. However, liquid water and other gases cannot permeate the breathable medium 436 and exit through the windows 435.

Additionally, the bottom surface 426 of the outer housing 418 defines an orifice 444 to connect the water dissipation device 412 to an input air source. The housing 418, therefore, defines a third flow path 446 from the orifice 444 through the water dissipation device 412 and out through the water vapor vents 434, or out through the windows 435. The third flow path 446 provides a route for air introduced by the auxiliary compressed dry air input source to blow condensation off of the breathable medium to reduce liquid water collecting in the water dissipation device, and increase the efficiency of the breathable permeable medium.

Figure 16:
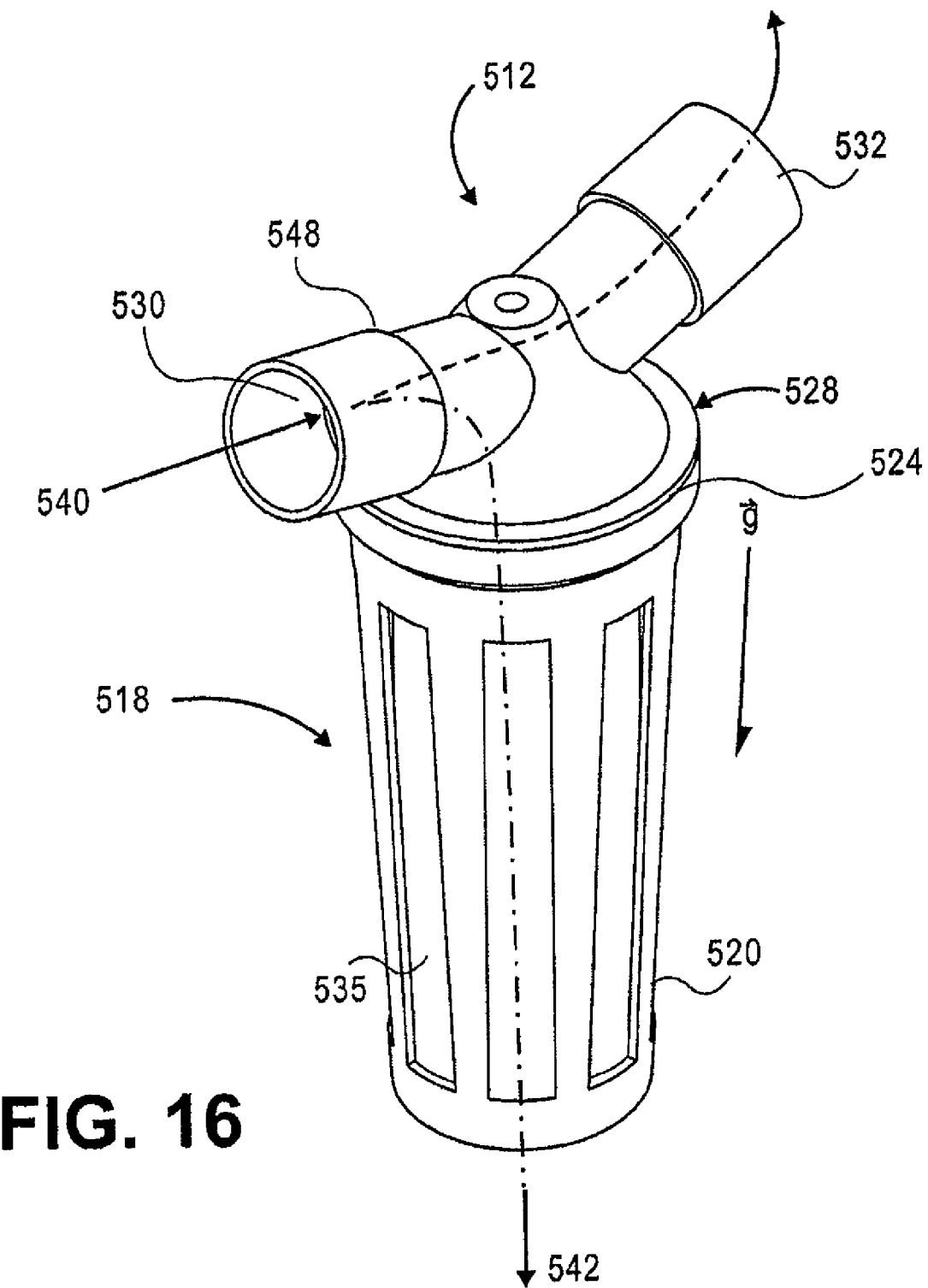
FIG. 16 is a three-quarter view illustrating another embodiment of the present invention.

Another embodiment of the present invention is illustrated in FIG. 16. FIG. 16 is a three-quarter view illustrating a water dissipation device 512 according to another embodiment of the present invention. In this embodiment, the housing 518 includes a caged cylindrical bottom container 520 that has side wall 522 defining a top opening 524. The housing also includes the lid 528 that is mounted on the top opening 524. Additionally, the housing 518 defines an entry port 130 and an exit port 532. As shown in the embodiment in FIG. 16, the side wall 522 of the caged cylindrical bottom container 520 defines a plurality of windows 535. An annular or tubular breathable medium is encased inside the cage structure of the housing 518 against the sidewalls 522. A first flow path 540 flows from the entry port 540 through to the exit port 532, while a second water vapor flow path 542 flows from the entry port 540 down into the housing 518 though a central channel defined by the annular breathable medium 536, and then out through the breathable medium 536 and the windows 535.

Figure 17:
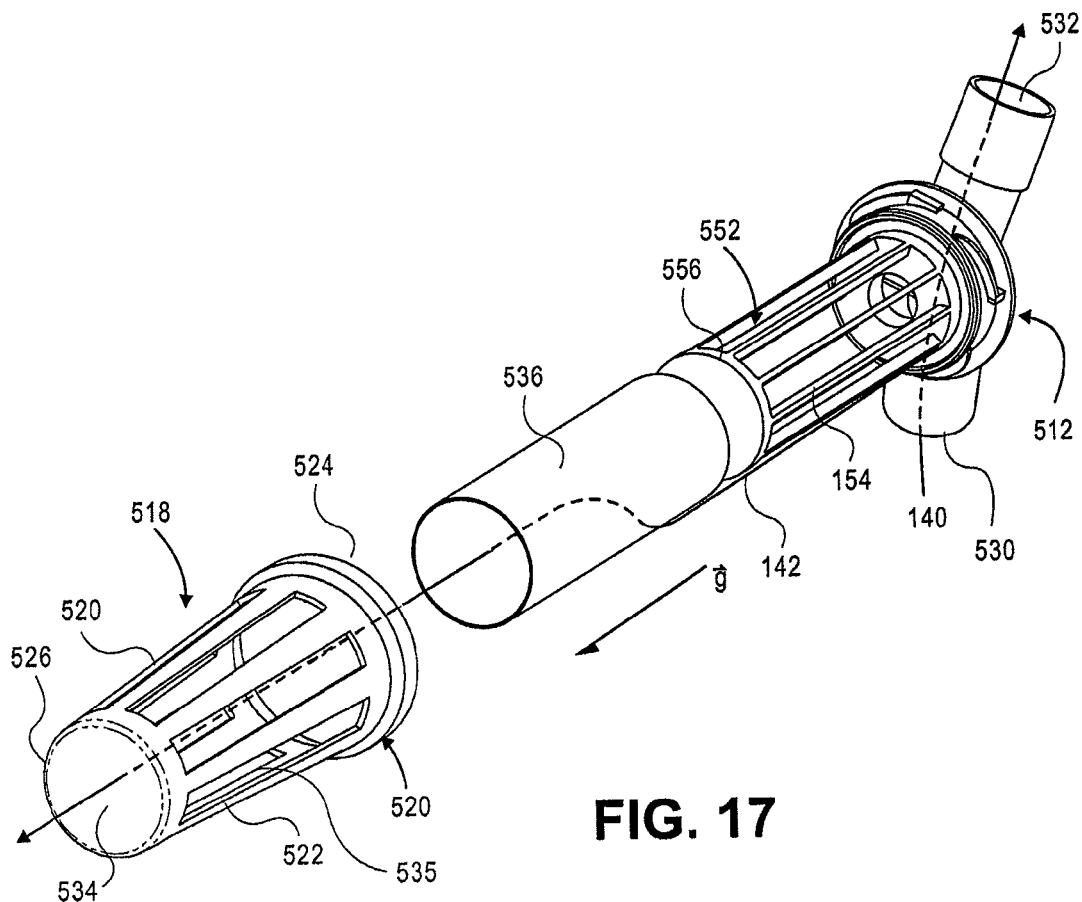
FIG. 17 is an exploded view of the embodiment illustrated in FIG. 16.

FIG. 17 is an exploded view of the embodiment illustrated in FIG. 16. FIG. 17 illustrates in more detail the structure of the housing 518 and the tubular breathable medium 536. Threads on the lid 528 as well as corresponding threads on the cylindrical bottom container 520 couple the lid 528 to the cylindrical bottom container 520.

Additionally, the lid 528 has a tubular cage 552 that extends into the cylindrical bottom container 520 of housing 518. The tubular cage 552 has fins 554 that extend along the span of the housing 518. The fins 554 are separated by longitudinal openings or spaces that define water vapor vents 556 between the fins 554. The tubular cage 552 has a flat disk 553 to form a bottom for the tubular cage 552. A tubular breathable medium 536 is also disposed within the cylindrical bottom container 520, and it is positioned between the tubular cage 552 and the cylindrical bottom container 520 of the outer housing 518.

Figure 18:
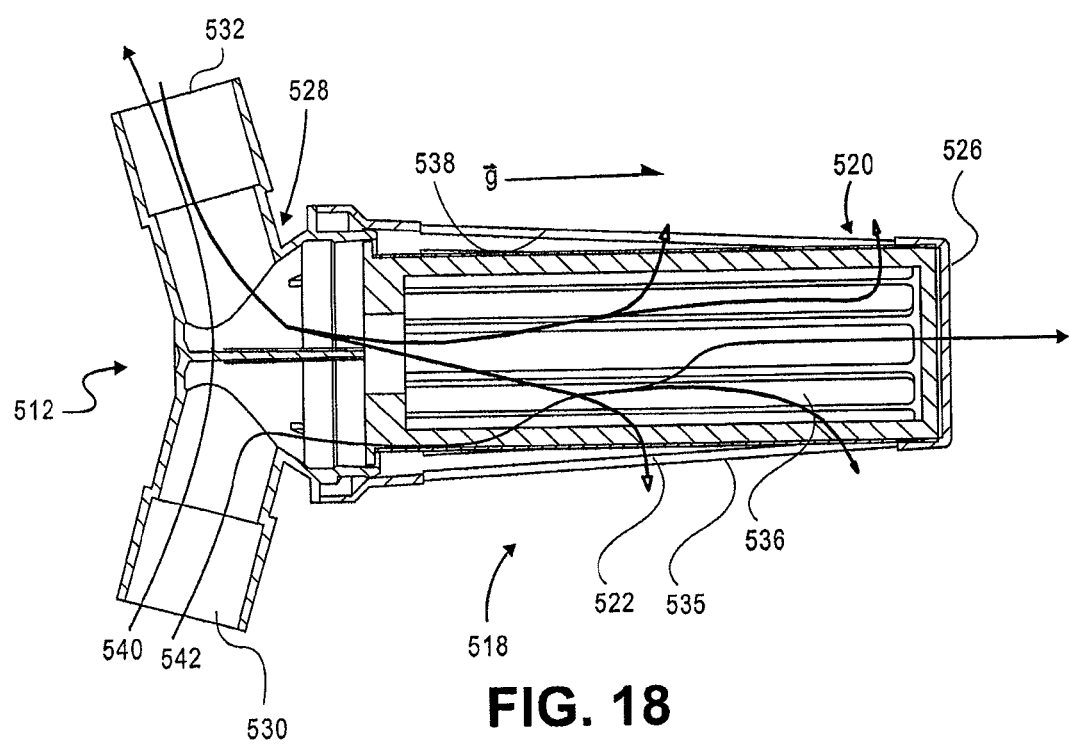
FIG. 18 is a cross-sectional view of the embodiment illustrated in FIGS. 16 and 17.

FIG. 18 is a cross sectional view of the embodiment illustrated in FIGS. 16 and 17. FIG. 18 illustrates the housing 518 and the breathable medium 536 in a fully assembled condition. The lid 528 and the cylindrical bottom container 520 couple together. The tubular cage 552 extends from a bottom surface of the lid 528 to the bottom surface 526 of the cylindrical bottom container 520. The tubular breathable medium 536 is disposed around and supported by the tubular cage 552.

A first flow path 540 is defined by the housing 518 and extends through the entry port 530, through the water dissipation device and through the exit port 532. The humidified gas generally flowing through the breathing circuit to which the device of the present invention is attached can therefore travel through the water dissipation device 512 via the first flow path 540. A second water vapor flow path 542 is also defined by housing 518 and extends from entry port 530 through tubular breathable medium 536 and out of the water dissipation device 512 via the water vapor vents 556 defined by the fins 554 of the tubular cage 552 and out through the windows 535 defined by the caged cylindrical bottom container 520. Water vapor in the humidified gas may permeate the breathable medium 536 to exit through the water vapor vents 556, but liquid water, bacteria, viruses and other gases cannot permeate the breathable medium 536. An alternative embodiment of the device shown in FIGS. 17 and 18 could also omit the bottom caged cylindrical housing body 520 such that the second flow path 542 flowed directly through breathable medium 536 out to the surroundings.

Figure 19:
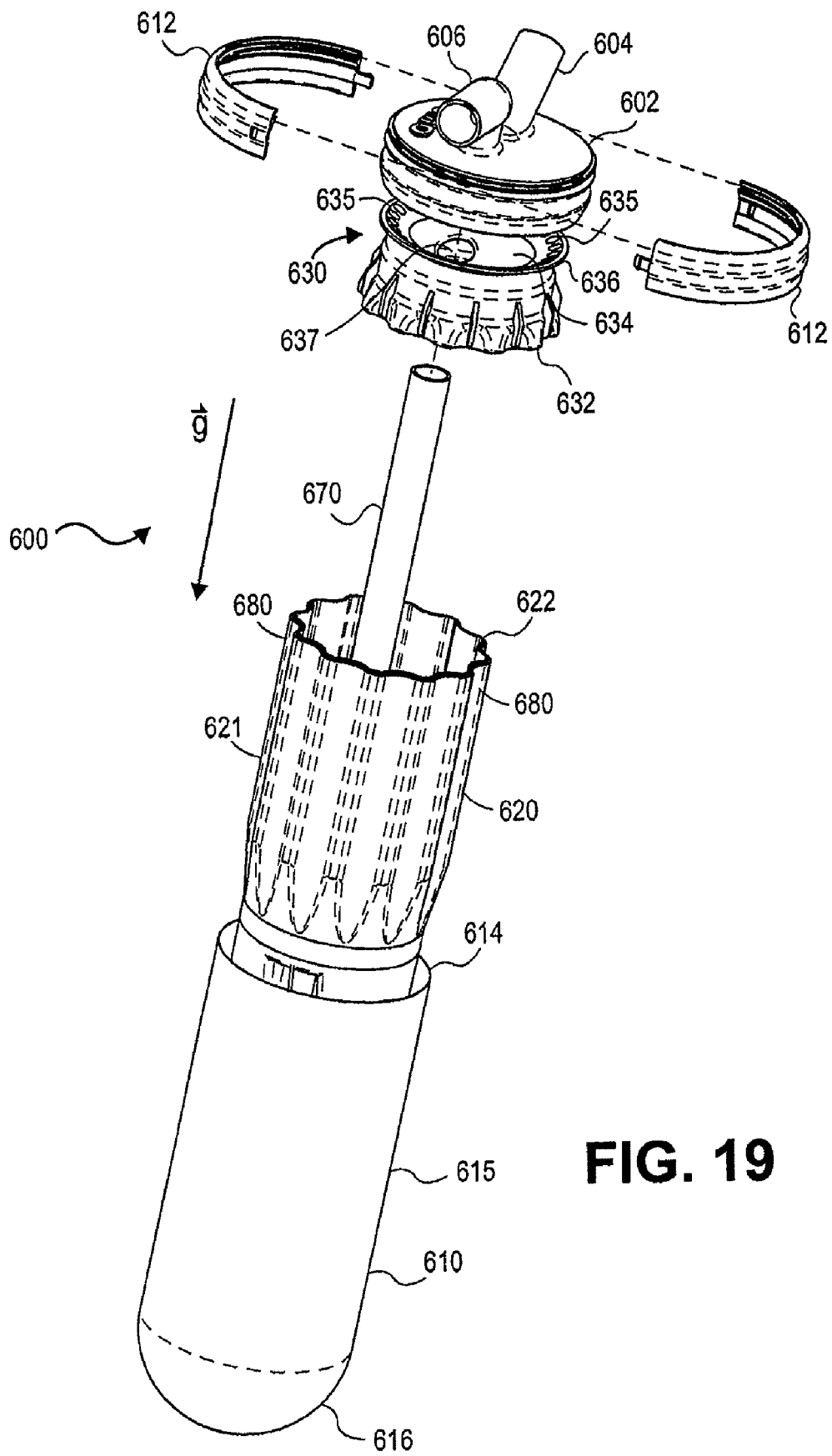
FIG. 19 is an exploded view of a water dissipation device in accordance with another embodiment of the invention.

FIG. 19 is an exploded view of a water dissipation device in accordance with another embodiment of the invention. The inventive device is shown relative to a gravity vector "g" as shown, such that "upper" and "lower" portions of the device are construed relative to said vector, "upper" being in the opposite direction from vector g, and "lower" being in the direction of vector g. The invention includes a water dissipation device 600 having an upper lid structure 602 defining an entry port 604 and an exit port 606 for coupling the device to a breathing circuit. The water dissipation device 600 is preferably placed at the end of the expiratory limb of a breathing circuit before the ventilator, although the positioning can be anywhere along a breathing circuit.

A cover or cover structure 610 is attached or coupled to the upper lid 602 via any means, but can include, in the embodiment shown in FIG. 19, a pair of semi-circular securing ring clamps or arc structures 612 which matingly fit around the perimeter of upper lid 602. The cover structure 610 is a cover element which can be described as a hollow, bag-shaped or bucket-shaped element defining a top opening 614 and closed bottom 616. The walls of cover structure 610 can have any width or thickness, but are relatively thin and can be flexible, such as a membrane. Alternatively, the cover structure 610 can be rigid and relatively inflexible. The material of cover structure 610 has a first inner layer made of water vapor wicking material, and a second outer layer surrounding the first inner layer, the second outer layer made of a water vapor breathable medium. The cover structure 610 is therefore a moisture accumulation and water vapor transfer means, providing a pathway for water vapor to exit a breathing circuit via flow into the water dissipation device 600 and through the cover structure 610.

The structural arrangement of the parts of the water dissipation device 610 are such that the device defines an inner flow space or series of flow spaces fluidly coupled to the entry port 604 and exit port 606. Furthermore, because of the water vapor breathable medium in the cover element 610, water vapor can also flow from inside of the device out to the environment surrounding the device, providing a flow path for water vapor to exit a breathing circuit to which the water dissipation device 610 is coupled. This provides a way to reduce the water vapor and moisture content which can build up in a breathing circuit when it is connected to a patient.

Figure 20:
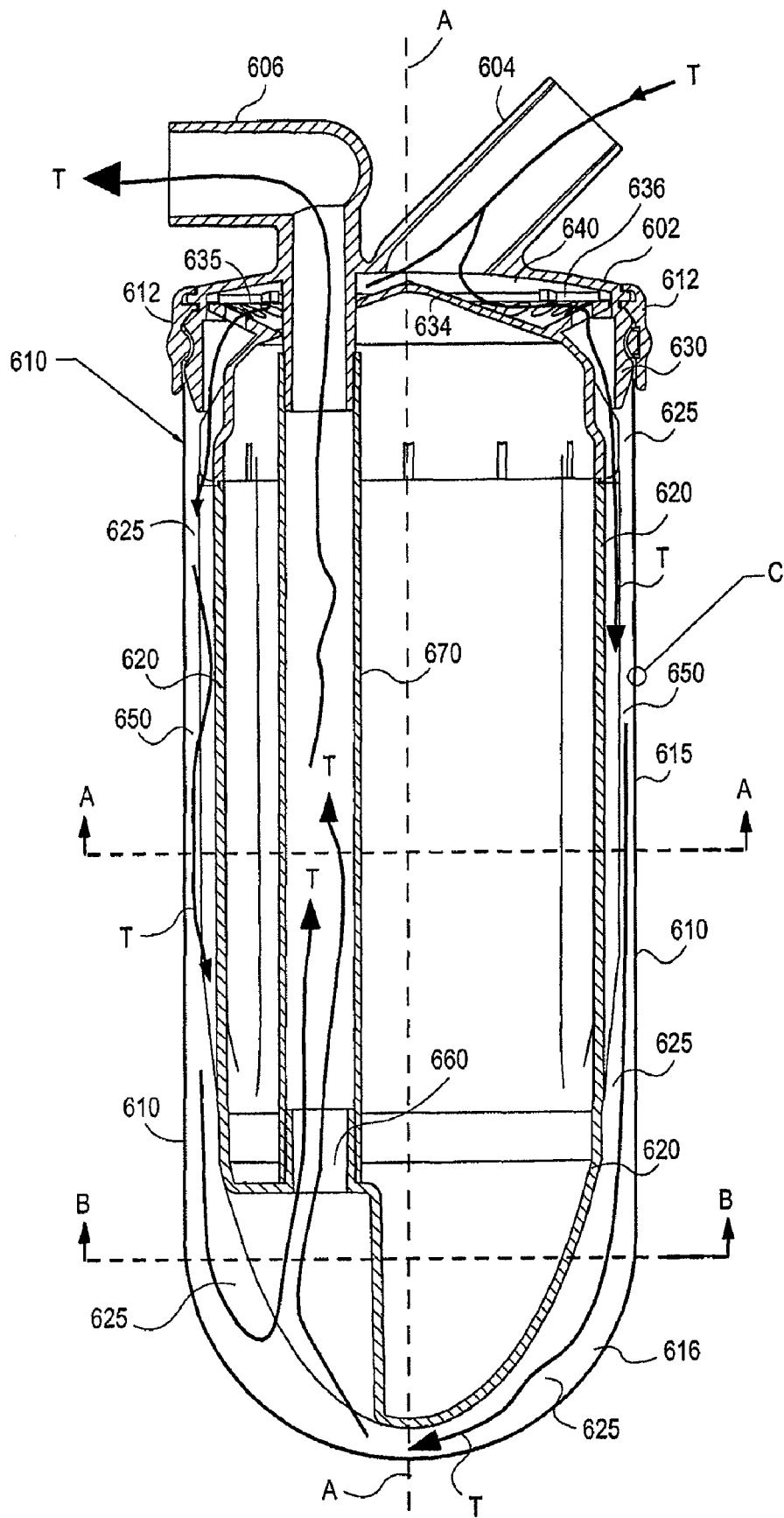
FIG. 20 is a cross-sectional view of the assembled water dissipation device shown in FIG. 19, showing some of the flow paths for fluid flowing through the device.

FIG. 20 is a cross-sectional view of the assembled water dissipation device 600, showing some of the flow paths for fluid flowing through the device. As also shown in FIG. 19, an inner frame element 620 is enclosed by the cover structure 610. The shape of the cover structure 610 is such that it narrowly surrounds the inner frame 620 to define an inner flow space 625 which is at least partially disposed between the inner frame and cover structure. The inner frame 620 is large enough relative to the cover structure 610 that is encloses a majority of a volume enclosed by the cover structure. This provides a set of narrow and annular flow spaces in the inner flow space 625 between the walls of the inner frame 620 and cover structure 610. The arrangement of the inner frame 620 inside of the cover structure 610 also reduces the overall volume or the inner flow space 625 and consequently the compliance of the device 600 when connected to a breathing circuit.

The flow paths provided by the inner flow space 625 are at least partially bounded by the inner layer of water vapor wicking material in the cover element 610. When the device 600 is coupled to a breathing circuit (not shown) via entry port 604, humidified gases flow through the inner flow space 625 along arrows T as shown in FIG. 20. The inner flow space 625 is tortuous and includes a number of different spaces and volumes all fluidly coupled together which wind around the inner frame 620. An upper cap 630 is also included which is positioned within the volume created when the upper lid 602 and cover element 610 are attached together. The upper cap 630 is shaped to have a lower end with a perimeter 632 which mates to the upper opening or perimeter 622 of the inner frame 620. The upper cap 630 is covered over its upper surface 634 by the upper lid 602 defining a volume or space 640 therebetween. Flow T from a breathing circuit coupled to the entry port 604 thereby flows through to the space 640 between the upper lid 602 and upper cap 630 and then impinges against upper surface 634 of the upper cap 630 and is radially distributed out from the central axis A to a plurality of holes 635 defined by a rim 636 on the perimeter of the upper cap 630. This distributes the flow T from the entry port 604 into a generally annular volume portion 650 of the inner flow space 625 defined between the inner frame 620 and cover 610. The upper cap 630 can therefore be characterized as an inner flow dispersal lid element disposed between the inner frame 620 and upper lid 602 and adjacent an upper end of the annular volume 650, the inner flow dispersal lid element 630 defining the plurality of openings 635 for dispersing flow received through the entry port 604 into the annular volume 650 of the inner flow space 625 of the device 600.

Figure 21:
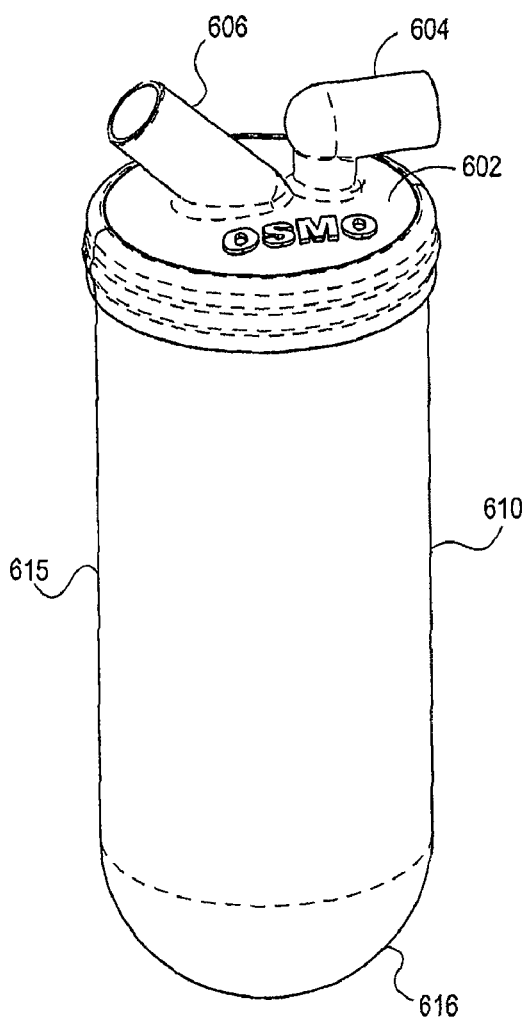
FIG. 21 is an exterior view of the assembled water dissipation device in FIG. 19.

As shown in FIG. 19, the cover structure 610 can have a substantially cylindrical portion 615 between its open top end 614 and closed bottom end 616 and the inner frame 620 can have a substantially cylindrical portion 621 enclosed by the substantially cylindrical portion 615 of the cover structure. By "substantially cylindrical" it is understood that deviations from a cylindrical shape are possible, such that elliptical, oval, rectangular, square, or other cross-sectional shapes are possible for the cover structure 610 and inner frame 620. In the preferred embodiment shown in FIGS. 19 and 20, the cover structure 610 and inner frame 620 are substantially cylindrical such that each element encloses a relatively large volume in relation to its outer surface area, in accordance with the geometric properties of a cylinder. FIG. 21 is an exterior view of the assembled water dissipation device 600 in FIG. 19.

Between the two substantially cylindrical elements 610 and 620 a substantial portion of the inner flow space 625 is disposed, including a plurality of long narrow flow spaces in an annular arrangement around central axis A of the device 600 shown in FIG. 20. The inner frame 620 also defines a lower opening 660 proximate the lower end 616 of the cover 610. As best shown in FIG. 20, the lower opening 660 is in fluid communication with the annular volume 650 and the exit port 606 defined by the upper lid 602 via a tube 670 which is surrounded by the inner frame 620. The inner frame 620 can further include a plurality of longitudinal ribs 680 along an outside surface of its cylindrical portion 621 which can, in one embodiment, support the cover element 610. The annular volume 650 can be separated into one or more longitudinal channels 685 defined between the inner frame 620 and cover element 610, each channel being longitudinally bounded by two longitudinal ribs 680. This is best shown in FIGS. 20A and 20B, which are transverse sectional views of the assembled water dissipation device shown in FIG. 19, taken along sections A-A and B-B, respectively, in FIG. 20.

Figure 20C:
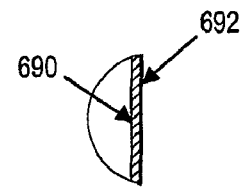
FIG. 20C is a schematic magnified view of a portion of the assembled water dissipation device shown in FIG. 19, taken from area C in FIG. 20.
Figure 20A:
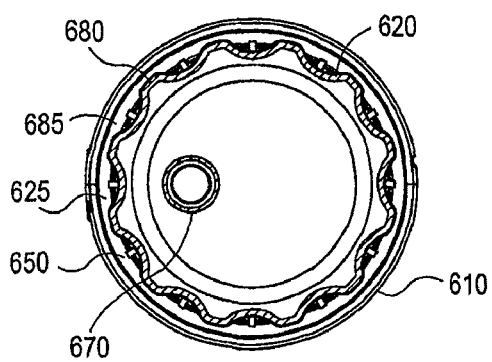
FIG. 20A is a transverse sectional view of the assembled water dissipation device shown in FIG. 19, taken along section A-A in FIG. 20.
Figure 20B:
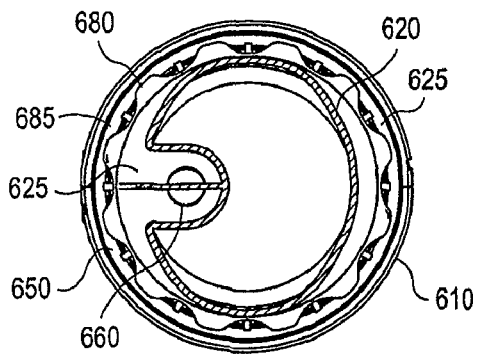
FIG. 20B is a transverse sectional view of the assembled water dissipation device shown in FIG. 19, taken along section B-B in FIG. 20.

FIG. 20C is a schematic magnified view of a portion of the walls of cover structure 610, taken from area C indicated in FIG. 20, which shows inner layer 690 of water vapor wicking material and outer layer 692 of water vapor breathable medium which make up cover structure 610. Both inner layer 690 and outer layer 692 are water vapor breathable in that both allow passage of water vapor. However inner layer 690 is made of wicking material which allows for adsorption and/or absorption of both moisture and water vapor in any phase, gas or liquid, using a capillary action, while the water vapor breathable medium of outer layer 692 permits the passage of water vapor only and not liquid water. Examples of wicking material in inner layer 690 are a knit or non-woven cloth or fabric, made of polyester, polyester and polypropylene blends, nylon, polyethylene or paper, and can be microfilaments or microfiber material such as Evolon® brand fabric material made by Freudenberg & Co. KG. A particular example of wicking material would be a non-woven material of 70% polypropylene and 30% polyester. Examples of outer layer 692 of water vapor breathable medium are Sympatex® brand water vapor permeable membranes made of polymers made by Sympatex Technologies. The wicking material can be laminated to the water vapor breathable medium to form a composite material.

The arrangement of flow spaces which are bounded by the cover structure 610 provides a relatively large surface area of the inner layer of water vapor wicking material in the cover structure 610 which bounds a substantial part of the inner flow space 625. In one embodiment of the present invention, the surface area of the cover structure 610 can vary in a range from 120 to 160 square inches. While the size of the cover structure 610 and overall device 600 is limited by the need for a reduced compliance when connected to a breathing circuit, it understood that the particular size of the present invention can be made to suit the needs of the patient. The arrangement of flow spaces in the present invention also provides a relatively long dwell time for fluid flow through the device 600 from the entry port 604 through to the exit port 606, since the fluid flowing from the entry port 604 is directed furthest away from the entry port 604 to the lower end portion of the device 600 at the lower end 616 of the cover 610, and then back through tube 670 to the exit port 606 to maximize the travel time of fluid flow through the device. Furthermore, the capillary action of the inner layer of water vapor wicking material causes moisture or water vapor to be adsorbed on the inner surface of cover structure 610 and absorbed into the inner layer, which water vapor or moisture then enters the second outer layer of the cover structure 610 which is made of a water vapor breathable material which allows water vapor to flow from within the device 600 out to the surroundings.

The present invention therefore provides a superior way of removal of moisture or water vapor from a breathing circuit, which is better than water traps or other fluid dissipation or moisture removal devices known in the prior art. The superior performance of the present invention is due to a number of factors, including one or more of: (i) the greater surface area of flow spaces 625 bounded by a water vapor breathable medium afforded by the arrangement of the structure of the device 600; (ii) the use of a water vapor wicking material in the inner layer of the cover element 610; and/or (iii) the relatively long dwell times and flow paths through the device 600 from the entry port 604 to the exit port 606. The result of the inventive apparatus disclosed is that when device 600 is connected to a breathing circuit, rainout or condensation in the breathing tube and collection of water within the breathing circuit is significantly reduced.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A water dissipation device for a breathing circuit, comprising:
    an entry port and an exit port for coupling the device to the breathing circuit, the entry port to receive fluid flow from the breathing circuit, the device further defining an inner flow space fluidly coupled to the entry port and exit port,
    a cover structure partially bounding the inner flow space and including
        an inner layer made of wicking material, and
        an outer layer over the inner layer, the outer layer made of a water vapor breathable medium which permits the passage of water vapor and does not permit the passage of liquid water.

2. The water dissipation device of claim 1, further comprising:
    an upper lid structure defining said entry port and exit port, and
    wherein the cover structure is a bucket-shaped structure having a closed bottom end and an open top end coupled to said upper lid structure, the inner flow space being enclosed by the cover structure and upper lid structure.

3. The water dissipation device of claim 2, further comprising:
    an inner frame enclosed by the cover structure, the inner flow space being partially disposed between the inner frame and cover structure, the inner frame enclosing a majority of a volume enclosed by the cover structure.

4. The water dissipation device of claim 3,
    wherein the cover structure has a substantially cylindrical portion between its open top end and closed bottom end and the inner frame has a substantially cylindrical portion enclosed by the substantially cylindrical portion of the cover structure.

5. The water dissipation device of claim 4,
    wherein the inner frame defines a lower opening proximate the closed bottom end of the cover structure, the device further comprising a conduit connecting the lower opening with the exit port, the conduit being surrounded by the inner frame.

6. The water dissipation device of claim 3,
wherein the inner frame includes a plurality of longitudinal ribs along an outside surface of its substantially cylindrical portion, the plurality of longitudinal ribs dividing a portion of the inner flow space into a plurality of flow channels between the inner frame and cover structure.

7. A water dissipation device for a breathing circuit, comprising:
a cover partially enclosing a flow space, said cover having at least two layers, including a first inner layer made of wicking material, and a second layer outside of and surrounding the first inner layer, the second layer made of a water vapor breathable medium which permits the passage of water vapor and does not permit the passage of liquid water;
an entry port for fluidly coupling the flow space to the breathing circuit, said flow space being at least partially bounded by the first inner layer,
the entry port, flow space and cover providing a flow path for water vapor out of the breathing circuit.

8. The water dissipation device of claim 7,
wherein the cover is bucket-shaped and defines a top opening coupled to an upper lid defining said entry port, the flow space being enclosed by the cover and upper lid and in fluid communication with the entry port.

9. The water dissipation device of claim 8, further comprising:
an inner frame enclosing a majority of the volume enclosed by the cover, the inner frame being surrounded by the cover, the flow space being partially disposed in an annular volume defined between the inner frame and cover,
wherein a lower end of the cover and the upper lid are disposed at respective lower and upper end portions of the device.

10. The water dissipation device of claim 9,
wherein the annular volume includes an upper end in fluid communication with the entry port defined by the upper lid, and further comprising:
an inner flow dispersal element disposed between the inner frame and upper lid and adjacent an upper end of the annular volume defining a plurality of openings for dispersing flow received through the entry port into the annular volume.

11. The water dissipation device of claim 9,
wherein the inner frame defines a lower opening proximate the lower end of the cover, the lower opening being in fluid communication with the annular volume and an exit port defined by the upper lid.

12. The water dissipation device of claim 9,
wherein the cover has a substantially cylindrical portion above its lower end and the inner frame has a substantially cylindrical portion enclosed by the substantially cylindrical portion of the cover.

13. A water dissipation device for a breathing circuit, comprising:
a hollow bucket-shaped thin flexible membrane composite cover structure defining a top opening and closed bottom and having walls made of a first inner layer made of wicking material, and a second outer layer surrounding the first inner layer, the second outer layer made of a water vapor breathable medium which permits the passage of water vapor and does not permit the passage of liquid water;
an upper lid covering said top opening and having an entry port for receiving flow from a breathing circuit;
an inner frame structure disposed inside a volume enclosed by the cover structure between the upper lid and closed bottom of the cover structure;
the cover structure enclosing a flow space for receiving flow from the entry port, said flow space being bounded by the upper lid, the first inner layer and the inner frame, the flow space being in fluid communication with the entry port and providing a flow path for water vapor flowing into the device from said entry port to exit the device from said volume through said cover structure.

14. The water dissipation device of claim 13, wherein the upper lid defines an exit port.

15. The water dissipation device of claim 13,
wherein the cover structure has a substantially cylindrical portion above its closed bottom and the inner frame structure has a substantially cylindrical annular portion enclosed by the substantially cylindrical portion of the cover structure.

* * * * *